United States Patent [19]

Oka et al.

[11] Patent Number: 5,830,149
[45] Date of Patent: Nov. 3, 1998

[54] PHYSICAL INFORMATION MONITOR SYSTEM HAVING MEANS FOR INDICATING AMOUNT OF DEVIATION OF MONITORED INFORMATION FROM NORMAL INFORMATION

[75] Inventors: Tohru Oka, Ichinomiya; Makoto Takakura, Sapporo, both of Japan

[73] Assignee: Colin Corporation, Komaki, Japan

[21] Appl. No.: 715,898

[22] Filed: Sep. 19, 1996

[30] Foreign Application Priority Data

Apr. 27, 1995 [JP] Japan .................................. 7-67272

[51] Int. Cl.⁶ ......................................................... A61B 5/02
[52] U.S. Cl. ........................... 600/500; 600/501; 600/492; 600/490
[58] Field of Search ...................................... 128/630, 666, 128/667, 668, 670, 672, 677–682, 687, 688; 600/300, 479, 480, 481, 483, 485, 490–495, 500, 501

[56] References Cited

U.S. PATENT DOCUMENTS

| | | |
|---|---|---|
| 3,168,592 | 2/1965 | Stewart . |
| 4,051,522 | 9/1977 | Healy et al. ............................. 128/903 |
| 5,054,495 | 10/1991 | Uemura et al. .......................... 128/680 |
| 5,103,831 | 4/1992 | Niwa ....................................... 128/687 |
| 5,355,889 | 10/1994 | Nevo et al. . |
| 5,406,954 | 4/1995 | Tomita .................................... 128/682 |
| 5,622,174 | 4/1997 | Yamazaki ................................ 600/441 |

FOREIGN PATENT DOCUMENTS

2 534 132  4/1984  France .
42 19 588  12/1992  Germany .

Primary Examiner—Jennifer Bahr
Assistant Examiner—Bryan K. Yarnell
Attorney, Agent, or Firm—Oliff & Berridge, PLC

[57] ABSTRACT

A physical information monitor system, including: (a) physical information obtaining component for successively obtaining physical information of a living subject; (b) physical information memory component for storing the physical information which is previously obtained in a comparatively normal condition of the living subject; (c) abnormality determining component for determining that the physical information obtained by the physical information obtaining component is abnormal if the physical information is outside a predetermined reference range; (d) a display device for indicating the physical information obtained by the physical information obtaining component; and (e) indication control component for controlling the display device to indicate, in a same indication area of the display device, the physical information which has been determined to be abnormal by the abnormality determining component and the physical information previously obtained in the comparatively normal condition of the subject and stored by the physical information memory component.

8 Claims, 5 Drawing Sheets

PHYSICAL INFORMATION MONITOR SYSTEM HAVING MEANS FOR INDICATING AMOUNT OF DEVIATION OF MONITORED INFORMATION FROM NORMAL INFORMATION

BACKGROUND OF THE INVENTION

1. Field of the Invention

The present invention relates to a physical information monitor system for monitoring successively obtained physical information of living subjects.

2. Discussion of the Related Art

For monitoring the physical condition of a patient (living subject) in an operating room or ICU (Intensive Care Unit), there is proposed a physical information monitor system adapted to successively measure one or more physical parameters of the patient, such as blood pressure, pulse rate, blood oxygen saturation and temperature, and to generate an abnormality signal indicative of abnormality of any physical parameter when the physical parameter is outside a predetermined reference range.

In general, the conventional physical information monitor system as described above has abnormality determining means for determining whether the obtained physical information is outside a predetermined reference range. The abnormality determining means generates an abnormality signal when the obtained physical information is outside the reference range. The abnormality signal may be visually indicated by suitable characters given on a display, or by a flickering or colored display area in which the measured abnormal value is displayed, for instance. Alternatively, the abnormality may be indicated by a sound or voice.

In the conventional physical information monitor system, however, the abnormality determining means simply generates the abnormality signal when the obtained physical information of the subject is outside the reference range. That is, the system is not arranged to indicate the degree of deviation of the obtained physical information from the reference range. In the conventional arrangement, it is impossible to judge whether the physical information slightly deviates from the reference range or considerably deviates from the reference range. Thus, in the conventional monitor system, it is difficult to quickly recognize the degree of abnormality of the physical information, i.e., the degree of emergency to deal with the abnormal physical condition of the patient upon generation of the abnormality signal.

SUMMARY OF THE INVENTION

It is therefore an object of the present invention to provide a physical information monitor system which permits easier recognition of the degree of abnormality or emergency of physical condition of the living subject upon occurrence of abnormality of the physical information of the patient.

The above object may be attained according to a principle of the present invention which provides a physical information monitor system comprising: (a) physical information obtaining means for successively obtaining physical information of a living subject; (b) physical information memory means for storing the physical information which is previously obtained in a comparatively normal condition of the living subject; (c) abnormality determining means for determining that the physical information obtained by the physical information obtaining means is abnormal if the physical information is outside a predetermined reference range; (d) a display device for indicating the physical information obtained by the physical information obtaining means; and (e) indication control means for controlling the display device to indicate, in a same indication area of the display device, the physical information which has been determined to be abnormal by the abnormality determining means and the physical information previously obtained in the comparatively normal condition of the subject and stored by the physical information memory means.

In the monitor system constructed according to the present invention, the physical information memory means stores the physical information previously obtained in the comparatively normal condition of the subject. When the abnormality determining means determines that the physical information obtained by the obtaining means is outside the predetermined reference range, the indication control means activates the display device to indicate the physical information which has been determined to be abnormal by the determining means and the physical information which was previously obtained in the comparatively normal condition and stored in the memory means, in the same indication area of the display device.

Since the abnormal physical information and the normal physical information are indicated in the same indication area of the display device as described above, the present arrangement permits easier recognition of the degree of abnormality of the physical information, namely, the degree of emergency to deal with the abnormal physical condition of the subject, by comparing the difference between the normal and abnormal physical information indicated in the same indication area.

According to a first preferred form of the present invention, the physical information obtaining means obtains as the physical information a series of pulses of a pulse wave generated in synchronism with heartbeat of the subject, while the indication control means controls the display device to indicate a series of pulses of a normal pulse wave previously obtained in the comparatively normal condition of the subject and the series of pulses of the pulse wave obtained by the physical information obtaining means in an abnormal condition of the subject, in a same two-dimensional coordinate system in which time is taken along an abscissa while an amplitude of the series of pulses is taken along an ordinate. This arrangement makes it possible to accurately compare the difference in the amplitude between the series of pulses of the normal pulse wave and the series of pulses of the abnormal pulse wave, since they are indicated in the same two-dimensional coordinate system.

According to a second preferred form of the present invention, the physical information obtaining means obtains as the physical information a series of pulses of a pulse wave generated in synchronism with heartbeat of the subject, while the indication control means controls the display device to indicate, in a same two-dimensional coordinate system, a waveform of one of a series of pulses of a normal pulse wave previously obtained in a comparatively normal condition of the subject and a waveform of one of a series of pulses of the pulse wave obtained by the physical information obtaining means in an abnormal condition of the subject, such that phases of the waveforms of the normal pulse wave and the abnormal pulse wave coincide with each other, in the same two-dimensional coordinate system in which time is taken along an abscissa while an amplitude of the series of pulses is taken along an ordinate. In this arrangement, the configuration of the pulse waveform of the abnormal pulse wave can be easily compared with that of the pulse waveform of the normal pulse wave.

According to one advantageous arrangement of the above second preferred form of the present invention, the indication control means includes normalizing means for normalizing the waveforms of the normal pulse wave and the abnormal pulse wave, such that at least one of an amplitude and a wavelength of the abnormal pulse wave coincides with the corresponding one of the amplitude and wavelength of the normal pulse wave, the indication control means controlling the display device to indicate the waveforms of the normal pulse wave and the abnormal pulse wave which have been normalized by the normalizing means, such that the waveforms of the normal pulse wave and the abnormal pulse wave are superimposed on each other. This arrangement permits easier recognition of the difference between the configuration of the pulse waveform of the normal pulse wave and the configuration of the pulse waveform of the abnormal pulse wave.

In the above advantageous arrangement of the present invention, the indication control means includes calculating means for calculating an area difference index which quantitatively indicates a difference between an area defined by the waveform of the normal pulse wave and an area defined by the waveform of the abnormal pulse wave, the indication control means controlling the display device to indicate the area difference index calculated by the calculating means. In this arrangement, the difference between the waveform of the normal pulse wave and the waveform of the abnormal pulse wave can be quantitatively recognized.

BRIEF DESCRIPTION OF THE DRAWINGS

The above and optional objects, features and advantages of the present invention will be better understood by reading the following detailed description of a presently preferred embodiment of the invention when considered in connection with the accompanying drawings in which.

DETAILED DESCRIPTION OF THE PREFERRED EMBODIMENT

Figure 1:
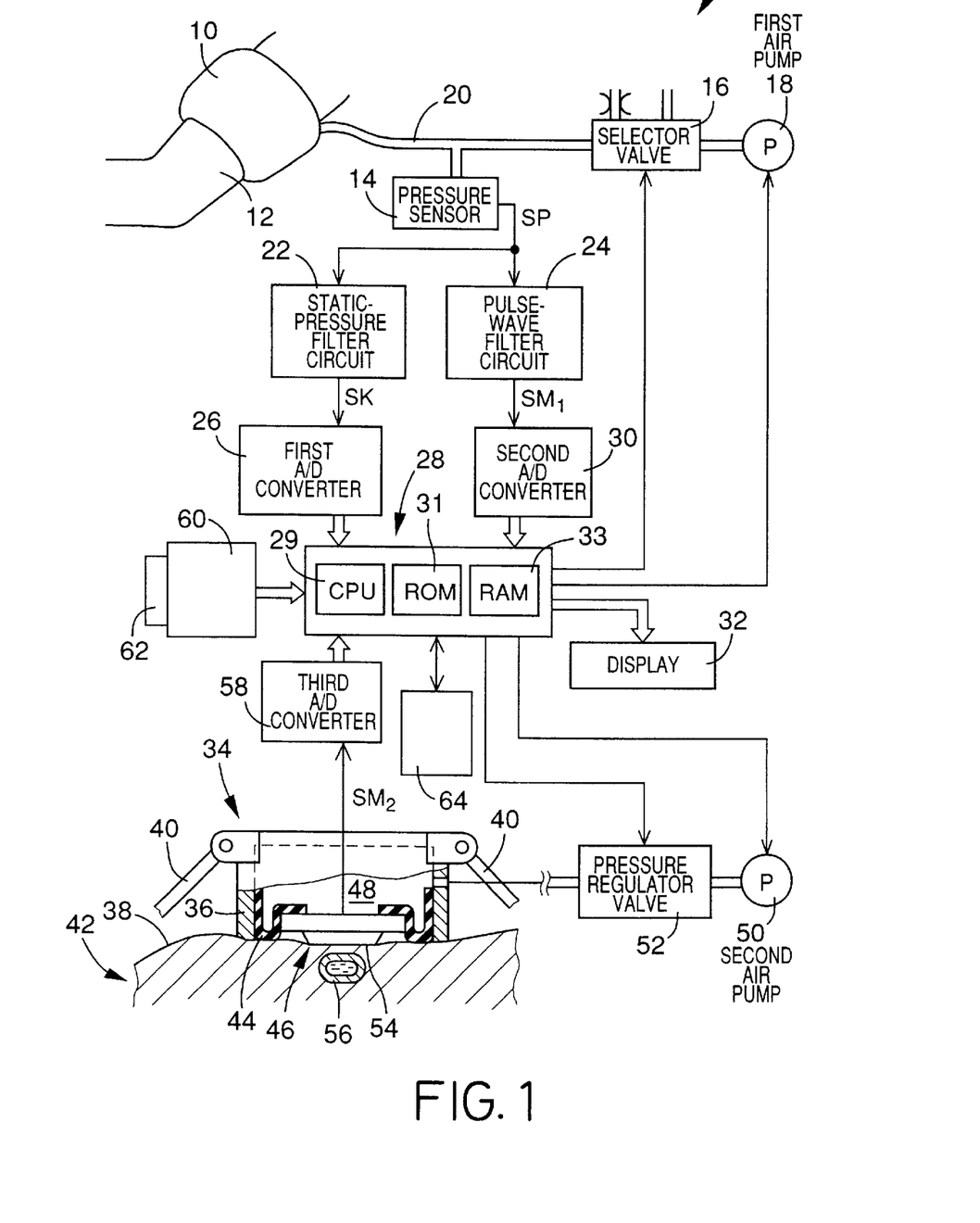
FIG. 1 is a diagrammatic block diagram of a blood pressure monitor system according to one embodiment of the present invention.

Referring first to FIG. 1, there is shown a blood pressure (BP) monitor system 8 constructed according to one embodiment of the present invention. In FIG. 1, the reference numeral 10 denotes an inflatable cuff constituted by an elongate fabric bag and a rubber bag accommodated in the elongate fabric bag. The cuff 10 is worn on a patient such that it is wound on an upper arm 12 of the patient, for example. A pressure sensor 14, a selector valve 16 and a first air pump 18 are connected to the cuff 10 via a conduit piping 20. The selector valve 16 is selectively placed in an inflation position, a slow-deflation position, and a rapid-deflation position. In the inflation position, the selector valve 16 permits pressurized air to be supplied from the first air pump 18 to the cuff 10. In the slow-deflation position, the selector valve 16 permits the pressurized air to be slowly discharged from the cuff 10. In the rapid-deflation position, the selector valve 16 permits the pressurized air to be rapidly discharged from the cuff 10.

The pressure sensor 14 detects an air pressure in the cuff 10 and supplies an electric signal SP representative of the detected pressure to a static-pressure filter circuit 22 and a pulse-wave filter circuit 24. The static-pressure filter circuit 22 has a low-pass filter and transmits a static component of the signal SP as a cuff-pressure signal SK to a control device 28 via a first analog to digital (A/D) converter 26.

The pulse-wave filter circuit 24 has a band-pass filter and transmits an oscillating component of the signal SP as a cuff pulse wave signal $SM_1$ to the control device 28 via a second analog to digital (A/D) converter 30. The cuff pulse wave signal $SM_1$ is representative of a pulse wave, i.e., an oscillatory pressure wave which is produced from a brachial artery of the patient in synchronism with the heartbeat of the patient and transmitted to the cuff 10. In the present embodiment, the cuff 10, pressure sensor 14 and pulse-wave filter circuit 24 cooperate with each other to function as a pulse wave sensor for obtaining the blood pressure of the patient.

The control device 28 is constituted by a so-called microcomputer which includes a central processing unit (CPU) 29, a read only memory (ROM) 31, a random access memory (RAM) 33 and an input and output (I/O) port not shown. The CPU 29 performs signal processing operations according to control programs stored in the ROM 31 by utilizing a temporary data storage function of the RAM 33, and generates drive signals through the I/O port so as to control the selector valve 16 and first air pump 18.

The present monitor system 8 further includes a pulse wave probe 34. The probe 34 is set on a wrist 42 located downstream of the arterial vessel of either one of the two upper arms 12, on which the cuff 10 is worn or is not worn. The probe 34 includes a container-like housing 36 which is detachably set on a body surface 38 of the wrist 42 with a pair of bands 40, 40 fastened round the wrist 42, such that the open end of the housing 36 contacts the body surface 38 of the wrist 42. A pulse wave sensor 46 is supported by the housing 36 via a flexible diaphragm 44, such that the pulse wave sensor 46 is displaceable relative to the housing 36 and is movable out of the housing 36 through its open end. The housing 36, diaphragm 44 and pulse wave sensor 46 cooperate with each other to define a pressure chamber 48, to which pressurized air is supplied from a second air pump 50 via a pressure regulator valve 52. Thus, the pulse wave sensor 46 is pressed against the body surface 38 with a pressing force $P_{HD}$ corresponding to an air pressure in the pressure chamber 48.

The pulse wave sensor 46 includes a plurality of semiconductor pressure-sensing elements (not shown) provided on one of opposite surfaces of a semiconductor substrate consisting of a single crystal of silicon, which one surface serves as a contact surface 54 of the pulse wave sensor 46. The pulse wave sensor 46 is pressed at the contact surface 54 against the body surface 38 of the wrist 42, to detect the oscillatory pressure wave, i.e., pulse wave, which is produced by a radial artery 56 and transmitted to the body surface 38 and the contact surface 54. The pulse wave sensor 46 generates a probe pulse wave signal SM2 representative of the detected pulse wave. The probe pulse wave signal SM2 is supplied to the control device 28 via a third analog to digital (A/D) converter 58.

The CPU 29 of the control device 28 operates according to the control programs stored in the ROM 31, for applying drive signals to the second air pump 50 and the pressure regulator valve 52 so as to adjust the air pressure in the pressure chamber 48, in other words, to adjust the pressing force $P_{HD}$ of the pulse wave sensor 46 which acts on the body surface 38. In monitoring the blood pressure of the patient, the CPU 29 determines an optimum pressing force $P_{HDP}$ of the pulse wave sensor 46, on the basis of the pulse waves obtained while the air pressure in the pressure chamber 48 is continuously changed. The pressure regulator valve 52 is controlled so as to maintain the air pressure in the pressure chamber 48 at an optimum level corresponding to the determined optimum pressing force $P_{HDP}$.

The present monitor system 8 further has a card reader 60 for reading information on a diagnostic information card 62 inserted therein. The card reader 60 is adapted to send the information to the control device 28. In the diagnostic information card 62, there are stored an identification code which identifies a specific living subject or patient (hereinafter referred to as "patient") and blood pressure data obtained during resting of the living subject when the patient received a medical diagnosis before the patient is subjected to blood pressure monitoring operation by the present BP monitor system 8. The memory device 64 is adapted to successively store the physical information obtained while the patient is in a normal condition during operation of the present monitor system 8.

Figure 3:
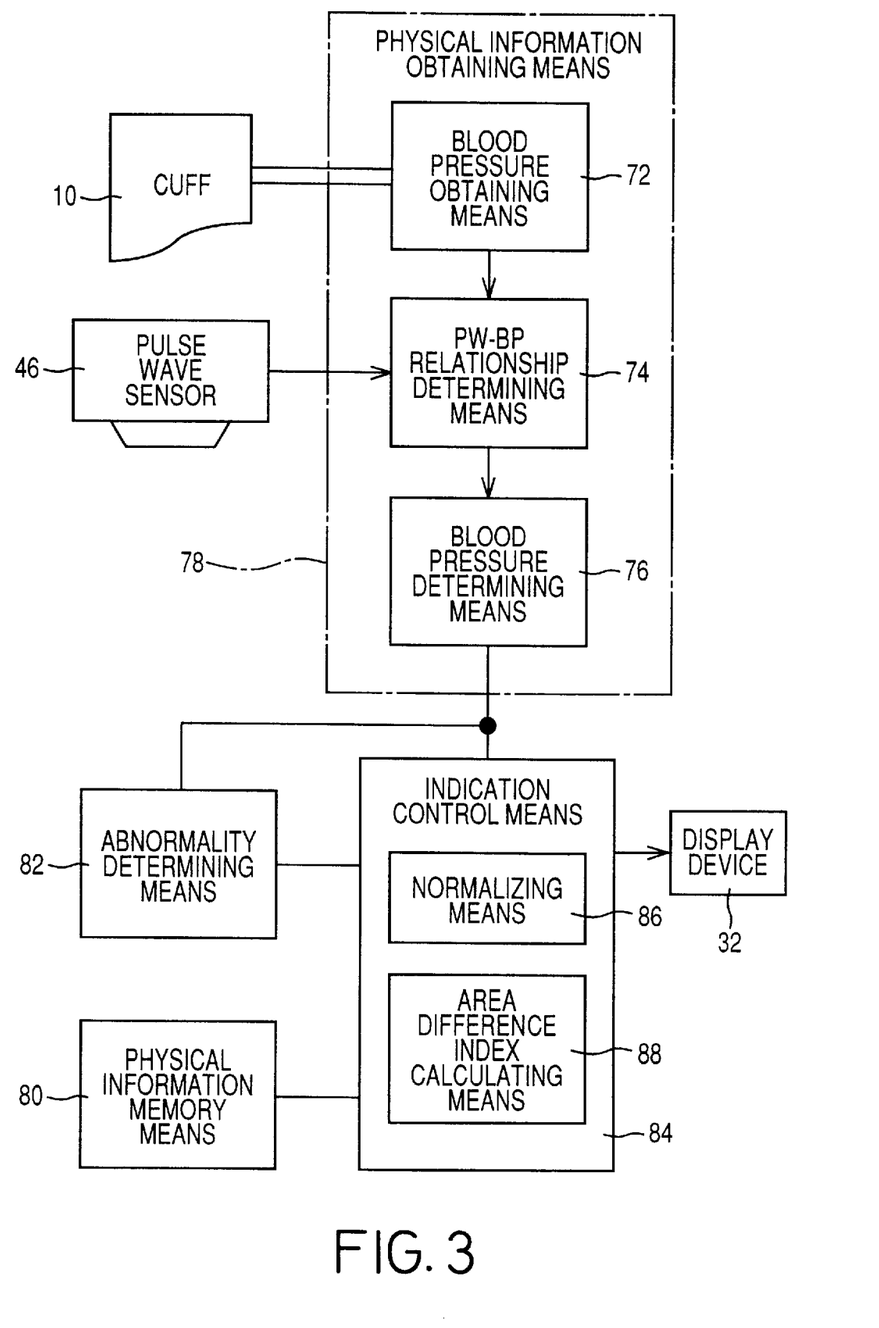
FIG. 3 is a block diagram schematically showing various functions of a control device used in the blood pressure monitor system of FIG. 1.

FIG. 3 illustrates various functions of the control device 28 of the present BP monitor system 8, which includes the above-indicated cuff 10, pulse wave sensor 46 and the card reader 60. The BP monitor system 8 further includes physical information obtaining means 78, physical information memory means 80 and abnormality determining means 82. The physical information obtaining means 78 incorporates blood pressure (BP) obtaining means 72, relationship determining means 74 and blood pressure determining means 76. The indication control means 84 incorporates normalizing means 86 and area difference index calculating means 88. The blood pressure (BP) obtaining means 72 is adapted to obtain a systolic blood pressure (SAP) and a diastolic blood pressure (DAP) of the patient according to a known oscillometric method (JIS T 1115). Described in detail, after the pressure in the cuff 10 is first increased up to a predetermined target value (e.g., about 180mmHg) higher by a suitable amount than an expected or estimated systolic blood pressure of the patient, the pressure in the cuff 10 is slowly lowered at a rate of about 3mmHg/sec. The SAP and DAP values are determined on the basis of a change in the magnitudes of successive pulses of the pulse wave obtained by the pulse-wave filter circuit 24 while the pressure in the cuff 10 is slowly lowered. When the blood pressure measurement is completed, the pressure in the cuff 10 is released.

The pulse wave sensor 46 is preferably worn on the wrist 42 of one of the arms 12 of the patient on which the cuff 10 is not wound, so that the pulse wave sensor 46 is pressed against the body surface 38 of the wrist 42 to detect the pulse wave generated from the radial artery of the wrist.

Figure 2:
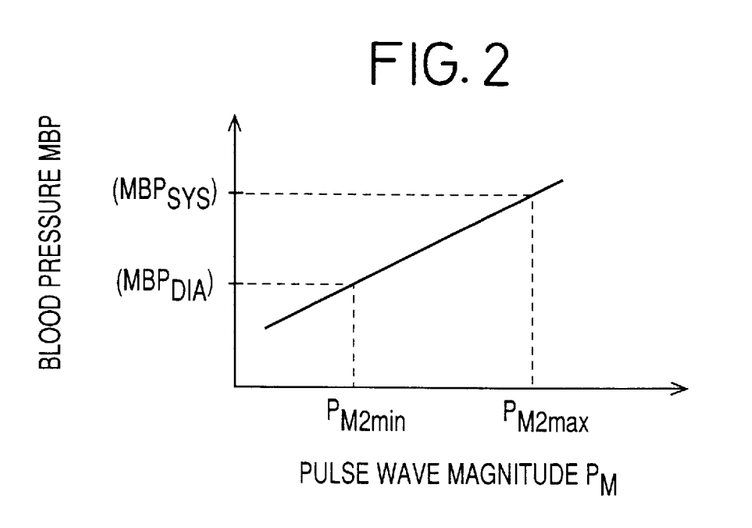
FIG. 2 is a graph representing a relationship between a pulse wave magnitude $P_M$ and a monitored blood pressure MBP.

The relationship determining means 74 of the physical information obtaining means 78 is adapted to determine a relationship between a magnitude PM of the pulse wave detected by the pulse wave sensor 46 and the blood pressure determined by the BP obtaining means 72. The relationship between the pulse wave magnitude PM and the blood pressure (hereinafter referred to as "PW–BP relationship") is indicated in a graph of FIG. 2 by way of example, and represented by the following equation:

$$MBP = A \cdot PM + B,$$

wherein MBP: monitored blood pressure;
A: a constant which represents a gradient; and
B: a constant which represents an intercept.

The blood pressure determining means 76 of the physical information obtaining means 78 is adapted to determine a monitored systolic blood pressure $MBP_{SYS}$ and a monitored diastolic blood pressure $MBP_{DIA}$ according to the determined PW–BP relationship, based on the magnitude PM of each pulse wave detected by the pulse wave sensor 46, i.e., on the basis of a maximum pulse wave magnitude (upper peak) $P_{M2max}$ and a minimum pulse wave magnitude (lower peak) $P_{M2min}$. The determined blood pressure values MBP ($MBP_{SYS}$ and $MBP_{DIA}$) are indicated on a display device 32, together with a pressure pulse wave indicative of the blood pressure of the patient, i.e., a waveform of the blood pressure. Thus, the physical information obtaining means 78 is adapted to obtain the blood pressure (BP) waveform as an example of the physical information of the living subject.

The physical information memory means 80 stores, in the memory device 64, the physical information in the form of the BP waveform indicative of the blood pressure of the patient obtained in the comparatively normal condition of the patient after the commencement of operation of the present system 8. The content of the memory device 64 is successively updated. The abnormality determining means 82 is adapted to determine whether the BP waveform is outside a predetermined reference range, e.g., a range of 70mmHg–150mmHg, and generates a signal indicative of abnormality of the blood pressure of the patient when the BP waveform is outside the reference range.

Figure 5:
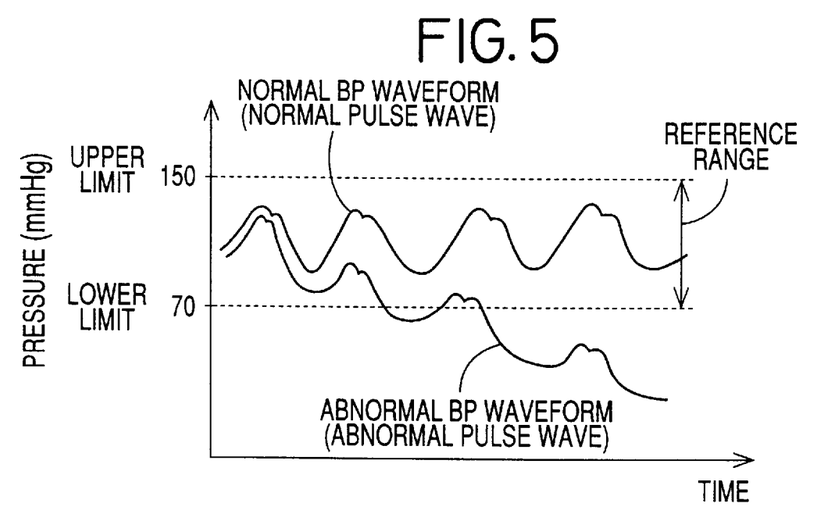
FIG. 5 is a view showing one example of waveform indication as a result of an operation of the monitor system of FIG. 1 according to the control routine of the flow chart of FIG. 4.

When the abnormality determining means 82 determines that the blood pressure represented by the blood pressure waveform (BP waveform) is abnormal, the indication control means 84 controls a display device 32 to indicate the BP waveform which was determined to be abnormal by the abnormality determining means 82 (abnormal BP waveform), together with the BP waveform (normal BP waveform) obtained in the comparatively normal condition of the patient and stored in the memory means 80, in the same indication area of the display device 32. FIG. 5 is a graph showing an example of an indication provided in the indication area of the display device 32, wherein the waveform of the normal blood pressure (i.e., the normal BP waveform) represented by a series of pulses of a normal pulse wave and the waveform of the abnormal blood pressure (i.e., the abnormal BP waveform) represented by a series of pulses of an abnormal pulse wave are indicated in the same two-dimensional coordinate system in which the time is taken along the abscissa while the magnitude of the pulses, i.e., the blood pressure is taken along the ordinate. It will be understood from the graph of FIG. 5 that the abnormal BP waveform can be compared with the normal BP waveform, so that the degree of abnormality of the blood pressure of the patient, namely, the degree of emergency to deal with the abnormal physical condition of the patient can be easily recognized.

Figure 6:
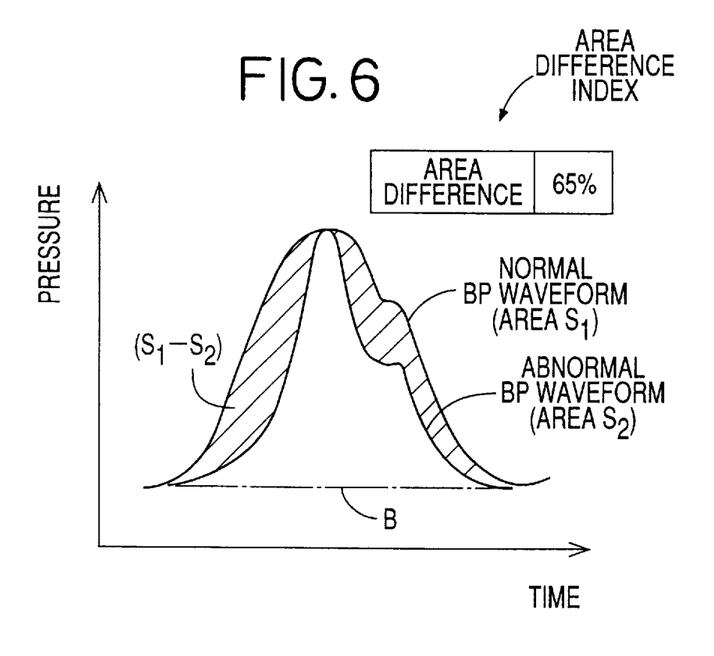
FIG. 6 is a view showing another example of waveform indication according to the control routine of FIG. 4.

The normalizing means 86 of the indication control means 84 is adapted to normalize the normal BP waveform and the abnormal BP waveform so that the peak amplitude and the wavelength of the abnormal BP waveform coincide with those of the normal BP waveform. The area difference index calculating means 88 is adapted to calculate an area difference index which quantitatively indicates a difference between an area S1 defined by one pulse of the normal BP waveform (i.e., one pulse waveform of the normal pulse wave) and a base line B indicated by a one-dot chain line in the graph of FIG. 5, and an area S2 defined by one pulse of the abnormal BP waveform (i.e., one pulse waveform of the abnormal pulse wave) and the base line B, after the normal and abnormal BP waveforms are normalized by the normalizing means 86. (Hereinafter the area S1 is referred to as "normal pulse waveform area S1" while the area S2 is referred to as "abnormal pulse waveform area S2".) The indication control means 84 controls the display device 32 to indicate the normal pulse waveform and the abnormal pulse waveform such that the two pulse waveforms are superimposed on each other in the same phase, that is, such that the reference points of the two pulse waveforms are aligned with each other in the directions of the amplitude and wavelength. The display device 32 also indicates the area difference index calculated by the calculating means 88. The area difference index may be represented as: (S1–S2) which is a difference between the normal pulse waveform area S1 and the abnormal pulse waveform area S2; S2/S1 (%) which is a ratio of the abnormal pulse waveform area S2 to the normal pulse waveform area S1; (S1–S2)/S1 (%) which is a ratio of the area difference (S2–S1) to the normal pulse waveform area S1. In FIG. 6, the area difference index S2/S1 (%) is indicated.

There will be described the operation of the control device 28 referring to the flow chart of FIG. 4.

Figure 4:
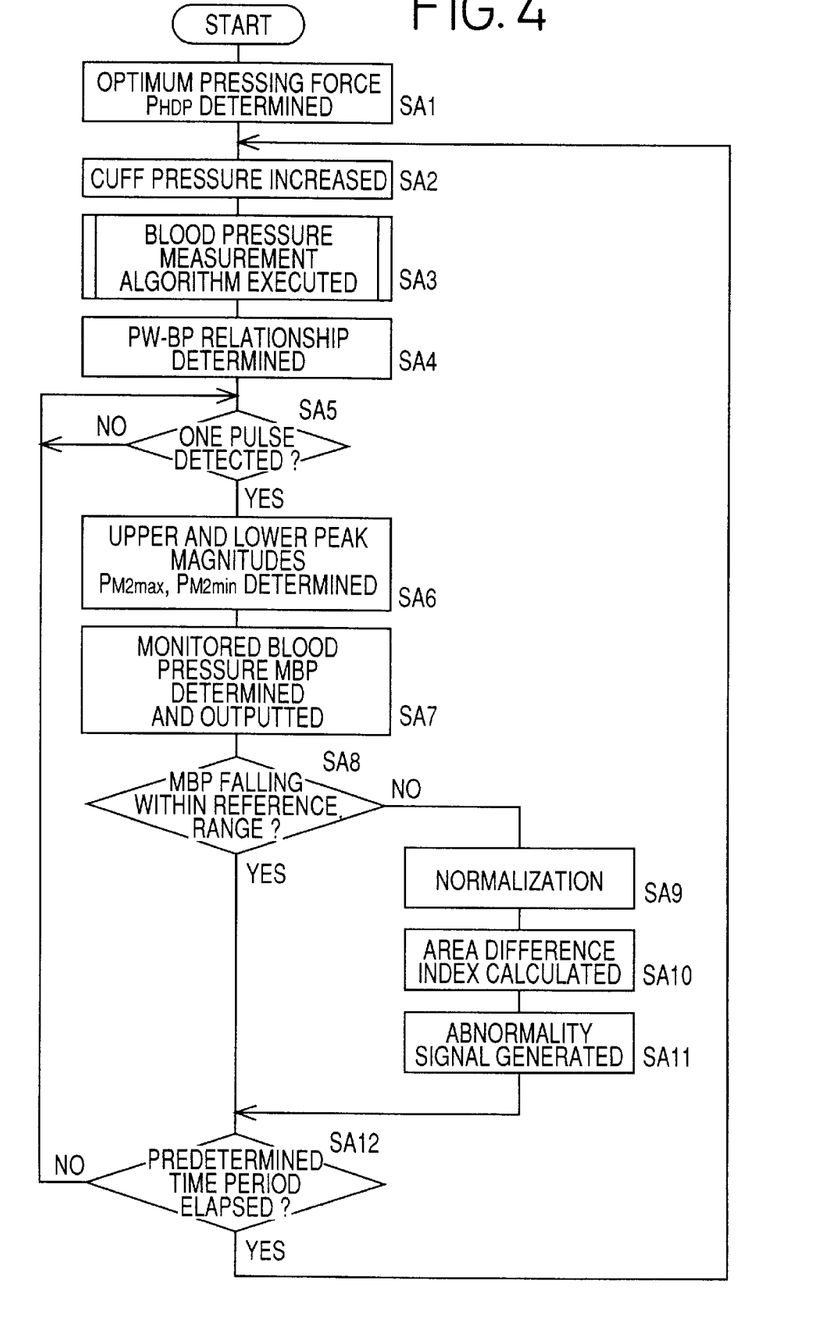
FIG. 4 is a flow chart representing a control routine executed by the control device in the blood pressure monitor system of FIG. 1.

A control routine illustrated in the flow chart of FIG. 4 is initiated with step SA1 in which the air pressure in the pressure chamber 48 is slowly raised, and the CPU 29 determines the optimum air pressure in the pressure chamber 48, at which the amplitude of a pulse detected by the pulse wave sensor 46 is maximized. The air pressure in the chamber 48 is held at the determined optimum level so that the pressing force of the pulse wave sensor 46 is maintained at the optimum value $P_{HDP}$.

Step SA1 is followed by step SA2 in which the pressure in the cuff 10 is raised for effecting the blood pressure measurement in the following step SA3 corresponding to the BP obtaining means 72. In this step SA3, the blood pressure of the patient is measured according to a predetermined blood pressure measuring algorithm. Described in detail, following the increase of the cuff pressure in step SA2, the selector valve 16 is placed in the inflation position and the first air pump 18 is actuated so as to increase the pressure in the cuff 10 up to a target value (e.g., 180mmHg) higher by a suitable amount than the estimated systolic blood pressure of the patient. Subsequently, the first air pump 18 is turned off and the selector valve 16 is switched from the inflation position to the slow-deflation position so as to slowly decrease the pressure in the cuff 10 at a rate of 3mmHg/sec. The systolic blood pressure (SAP), mean blood pressure (MAP) and diastolic blood pressure (DAP) are determined based on variation of the amplitudes of successive pulses of the cuff pulse wave signal SM1 obtained during the slow decreasing of the cuff pressure, according to a well-known oscillometric blood pressure determining algorithm, for example. Further, the pulse rate (PR) is determined based on an interval between successive adjacent pulses of the cuff pulse wave signal SM1. The determined SAP, MAP, DAP and PR values are indicated on the display 32, and the selector valve 16 is switched from the slow-deflation position to the rapid-deflation position, whereby the pressure in the cuff 10 is rapidly lowered.

The control flow then goes to step SA4 corresponding to the PW–BP relationship determining means 74 so as to obtain a relationship between the magnitude (absolute value) of each pulse of the pulse wave detected by the pulse wave sensor 46 (i.e., magnitude of the probe pulse wave signal SM2) and the blood pressure values SAP, DAP measured by using the cuff 10 in step SA3. In other words, one pulse of the probe pulse wave signal SM2 from the pulse wave sensor 46 is read to determine a maximum and a minimum magnitude $P_{M2max}$, $P_{M2min}$ of that pulse. Subsequently, the PW–BP relationship determining means 74 determines the relationship between the pulse wave magnitude PM and the monitored blood pressure MBP as indicated in the graph of FIG. 2, on the basis of the determined maximum and minimum pulse wave magnitudes $P_{M2max}$, $P_{M2min}$, and the systolic and diastolic blood pressure values SAP, DAP obtained by using the cuff 10 in step SA3.

Step SA4 is followed by step SA5 to determine whether one pulse of the probe pulse wave signal SM2 has been supplied from the pulse wave sensor 46. As long as a negative decision is obtained in step SA5, this step is repeatedly implemented. If an affirmative decision is obtained in step SA5, the control flow goes to steps SA6 and SA7 corresponding to the blood pressure determining means 76, so as to determine the maximum and minimum magnitudes (upper and lower peaks) of the pulse of the probe pulse wave signal SM2 received from the pulse wave sensor 46 which is pressed against the body surface 38 with the above-described optimum pressing force $P_{HDP}$. Further, a monitored systolic blood pressure $MBP_{SYS}$ and a monitored diastolic blood pressure $MBP_{DIA}$ are determined based on the maximum and minimum magnitudes $P_{M2max}$ and $P_{M2min}$ of the pulse of the probe pulse wave signal SM2, according to the PW–BP relationship (as shown in the graph of FIG. 2) which has been obtained in step SA4 as described above. The determined monitored systolic and diastolic blood pressure values $MBP_{SYS}$ and $MBP_{DIA}$ are indicated on the display device 32, together with a series of pulses of the pulse wave calibraled or determined according to the above-described PW–BP relationship, i.e., together with a blood pressure (BP) waveform.

The control flow then goes to step SA8 corresponding to the abnormality determining means 82 to determine whether the monitored blood pressure determined in step SA7 falls within the predetermined reference range. The reference range used for determining whether the blood pressure of the living subject is abnormal is suitably determined by the upper limit (systolic blood pressure $MBP_{SYS}$) of 150mmHg and the lower limit (diastolic blood pressure $MBP_{DIA}$) of 70mmHg.

If a negative decision is obtained in step SA8, this means that the blood pressure of the patient is abnormal, and the control flow goes to step SA9 corresponding to the normalizing means 86 so as to implement the normalization for superimposing the abnormal pulse wave and the normal pulse wave on each other such that the reference points of the abnormal and normal pulse waves are aligned with each other in the directions of the amplitude and wavelength. Then, the control flow goes to step SA10 corresponding to the area difference index calculating means 88 to calculate, as the area difference index, either one of: (S1–S2) which is a difference between the normal pulse waveform area S1 and the abnormal pulse waveform area S2; S2/S1 (%) which is a ratio of the abnormal pulse waveform area to the normal pulse waveform area; and (S1–S2)/S1 (%) which is a ratio of the area difference (S1–S2) to the normal pulse waveform area S1.

Step SA10 is followed by step SA11 to generate the abnormality signal indicative of the abnormal blood pressure of the patient. The abnormality is visually indicated on the display device 32, for instance, by a flickering, colored or enlarged area of the display screen. Alternatively, the abnormality is indicated by an audible alarm device adapted to generate a sound or voice, or by other devices adapted to inform the abnormal blood pressure of the patient. The display device 32 is controlled to indicate the normal pulse wave and the abnormal pulse wave in the same coordinate system as shown in FIGS. 5 and 6, together with the area difference index calculated by the calculating means 88.

Step SA11 is followed by step SA12. This step SA12 is effected immediately following step SA8 if an affirmative decision is obtained in step SA8. Step SA12 is provided to determine whether a predetermined time period has elapsed after the commencement of the blood pressure measurement by using the cuff 10 in step SA3. For example, the predetermined time period is several tens of minutes. If a negative decision is obtained in step SA12, the control flow goes back to step SA5 and the following steps for determining the monitored systolic and diastolic blood pressure $MBP_{SYS}$ and $MBP_{DIA}$ of the pulse wave signal SM2 and indicating the determined blood pressures $MBP_{SYS}$ and $MBP_{DIA}$ on the display device 32. On the other hand, if an affirmative decision is obtained in step SA12, the control flow goes back to step SA2 and the following steps so as to update the PW–BP relationship.

According to the present embodiment described above, the memory device 64 corresponding to the physical information memory means 80 stores the BP waveform indicative of the blood pressure obtained in a comparatively normal condition of the patient. When the abnormality determining means 82 corresponding to step SA8 determines that the BP waveform obtained during the current monitoring operation is outside the reference range, the indication control means 84 corresponding to steps SA9 and SA10 controls the display device 32 to indicate the BP waveform which is determined to be abnormal by the abnormality determining means 88 (abnormal BP waveform), and the BP waveform (normal BP waveform) which was obtained in the comparatively normal condition and stored in the memory device 64, in the same indication area of the display device 32. This arrangement permits the medical workers to easily recognize the degree of abnormality of the blood pressure of the patient, i.e., the degree of emergency to deal with the abnormal physical condition of the patient, simply by comparing the normal BP waveform and the abnormal BP waveform which are indicated in the same display area.

According to the present embodiment, the indication control means 84 controls the display device 32 to indicate a series of pulses of the normal pulse wave (the normal BP waveform indicative of the normal blood pressure of the patient) and a series of pulses of the abnormal pulse wave (the abnormal BP waveform indicative of the abnormal blood pressure of the patient), in the same two-dimensional coordinate system in which the time is taken along the abscissa while the magnitude of the pulses, i.e., the blood pressure is taken along the ordinate. This arrangement assures accurate comparison between the magnitude or amplitude of the normal pulse wave (the pressure difference between the systolic blood pressure and the diastolic blood pressure), i.e., pulse pressure, and the magnitude or amplitude of the abnormal pulse wave.

The indication control means 84 further controls the display device 32 to indicate one pulse waveform of the normal pulse wave (normal BP waveform) and one pulse waveform of the abnormal pulse wave (abnormal BP waveform), such that the phases of the two pulse waveforms coincide with each other as shown in the graph of FIG. 6. This arrangement permits easier comparison between the normal and abnormal pulse waveforms.

The indication control means 84 includes the normalizing means 86 for normalizing the normal and abnormal pulse waves such that at least one of the amplitude and wavelength of the abnormal pulse wave coincide with the corresponding one of the amplitude and wavelength of the normal pulse wave. After the normal and abnormal pulses are normalized by the normalizing means 86, the display device 32 indicates one pulse waveform of the normal pulse wave and the corresponding pulse waveform of the abnormal pulse wave, such that the normal and abnormal pulse waveforms are superimposed on each other. Thus, the difference between the configurations of the normal and abnormal pulse waveforms can be easily recognized.

The indication control means 84 further includes the area difference index calculating means 88 for calculating the area difference index which numerically indicates the difference between the area defined by the above-indicated one normal pulse waveform and the area defined by the above-indicated one abnormal pulse waveform, after the pulses are normalized by the normalizing means 86. The calculated area difference index is also graphically indicated on the display device 32, so that the difference between the configurations of the normal and abnormal pulse waveforms can be quantitatively recognized.

While the present invention has been described in its presently proffered embodiment, it is to be understood that the invention may be otherwise modified.

In the illustrated embodiment, a series of pulses of the normal pulse wave and a series of pulses of the abnormal pulse wave are indicated in the same coordinate system as shown in FIG. 5, and one normal pulse waveform and one abnormal pulse waveform which are superimposed on each other are indicated in the same coordinate system as shown in FIG. 6, so that the normal and abnormal pulse waves can be easily compared with each other. However, the advantage of the present invention can be similarly attained when the display device 32 is adapted to provide only one of the graphical representations as shown in FIGS. 5 and 6. If the display device 32 is adapted to provide only the graphical representation of FIG. 5, the normalizing means 86 and the area difference index calculating means 88 may be eliminated.

The reference range used in step SA8 for determining the abnormality of the blood pressure may be automatically determined on the basis of the blood pressure obtained in a comparatively normal condition of the patient. The determination of the abnormality of the blood pressure may be effected when either one of the systolic blood pressure (SAP), mean blood pressure (MAP) and diastolic blood pressure (DAP) is outside the corresponding reference range.

In the illustrated embodiment, the blood pressure is monitored as the physical information. However, the blood pressure may be replaced with blood oxygen saturation, temperature, pulse rate or fluctuation of these parameters (in a given time period).

The blood pressure obtaining means 72 is adapted to determine the blood pressure according to the known oscillometric method, based on a change in the magnitude of the pulses of the pulse wave, which change is detected as the pressure in the cuff 10 is varied. However, the blood pressure obtaining means 72 may be adapted to determine the blood pressure according to the known Korotkoff-sound method in which a microphone is used to detect presence and absence of Korotkoff sounds of an artery as the pressure in the cuff 10 is changed.

It is to be understood that the present invention may be embodied with other changes, improvements and modifications which will occur to those skilled in the art without departing from the scope and spirit of the invention defined in the appended claims.

What is claimed is:

1. A physical information monitor system, comprising:

physical information obtaining means for successively obtaining physical information of a living subject, said physical information obtaining means obtaining as said physical information a series of pulses of a pulse wave generated in synchronism with heartbeat of said subject;

physical information memory means for storing said physical information which is previously obtained in a comparatively normal condition of said living subject;

abnormality determining means for determining that said physical information obtained by said physical information obtaining means is abnormal when said physical information is outside a predetermined reference range;

a display device for indicating said physical information obtained by said physical information obtaining means; and indication control means for controlling said display device to simultaneously indicate, while the physical information is abnormal, in a same indication area of said display device, said physical information which has been determined to be abnormal by said abnormality determining means and said physical information previously obtained in said comparatively normal condition of said subject and stored by said physical information memory means, said indication control means controlling said display device to indicate, in a same two-dimensional coordinate system, a waveform of one of a series of pulses of a normal pulse wave previously obtained in a comparatively normal condition of said subject and a waveform of one of a series of pulses of the pulse wave obtained by said physical information obtaining means in an abnormal condition of said subject, such that phases of said waveforms of said normal pulse wave and said abnormal pulse wave coincide with each other, in said same two-dimensional coordinate system in which time is taken along an abscissa while an amplitude of said series of pulses is taken along an ordinate, said indication control means including normalizing means for normalizing said waveforms of said normal pulse wave and said abnormal pulse wave, such that at least one of an amplitude and a wavelength of said abnormal pulse wave coincides with the corresponding one of the amplitude and wavelength of said normal pulse wave, said indication control means controlling said display device to indicate the waveforms of said normal pulse wave and said abnormal pulse wave which have been normalized by said normalizing means, such that said waveforms of said normal pulse wave and said abnormal pulse wave are superimposed on each other, said indication control means including calculating means for calculating an area difference index which quantitatively indicates a difference between an area defined by said waveform of said normal pulse wave and an area defined by said waveform of said abnormal pulse wave, said indication control means controlling said display device to indicate said area difference index calculated by said calculating means.

2. A physical information monitor system according to claim 1, wherein said physical information obtaining means obtains as said physical information a series of pulses of a pulse wave generated in synchronism with heartbeat of said subject, while said indication control means controls said display device to indicate a series of pulses of a normal pulse wave previously obtained in the comparatively normal condition of said subject and said series of pulses of the pulse wave obtained by said physical information obtaining means in an abnormal condition of said subject, in a same two-dimensional coordinate system in which time is taken along an abscissa while an amplitude of said series of pulses is taken along an ordinate.

3. A physical information monitor system according to claim 1, wherein said physical information obtaining means comprises:

pulse wave detecting means for detecting said series of pulses of said pulse wave generated in synchronism with heartbeat of said subject;

blood pressure obtaining means including an inflatable cuff, for obtaining a blood pressure of said living subject;

relationship determining means for determining a relationship between a magnitude of said pulse wave detected by said pulse wave detecting means and said blood pressure obtained by said blood pressure obtaining means; and blood pressure determining means for determining a monitored systolic blood pressure ($MBP_{SYS}$) and a monitored diastolic blood pressure ($MBP_{DIA}$) based on said magnitude of said pulse wave and said relationship determined by said determining means.

4. A physical information monitor system according to claim 1, wherein said physical information comprises blood pressure of said living subject.

5. A physical information monitor system according to claim 1, wherein said physical information stored in said physical information memory means comprises an average of a plurality of previously obtained physical information values.

6. A physical information monitor system, comprising:

physical information obtaining means for successively obtaining physical information of a living subject, said physical information obtaining means obtaining as said physical information a series of pulses of a pulse wave generated in synchronism with heartbeat of said subject;

physical information memory means for storing said physical information which is previously obtained in a comparatively normal condition of said living subject;

abnormality determining means for determining that said physical information obtained by said physical information obtaining means is abnormal when said physical information is outside a predetermined reference range;

a display device for indicating said physical information obtained by said physical information obtaining means; and indication control means for controlling said display device to simultaneously indicate, while the physical information is abnormal, in a same indication area of said display device, said physical information which has been determined to be abnormal by said abnormality determining means and said physical information previously obtained in said comparatively normal condition of said subject and stored by said physical information memory means, said indication control means controlling said display device to indicate, in a same two-dimensional coordinate system, a waveform of one of a series of pulses of a normal pulse wave previously obtained in a comparatively normal condition of said subject and a waveform of one of a series of pulses of the pulse wave obtained by said physical information obtaining means in an abnormal condition of said subject, such that phases of said waveforms of said normal pulse wave and said abnormal pulse wave coincide with each other, in said same two-dimensional coordinate system in which time is taken along an abscissa while an amplitude of said series of pulses is taken along an ordinate, said indication control means including normalizing means for normalizing said waveforms of said normal pulse wave and said abnormal pulse wave, such that an amplitude and a wavelength of said abnormal pulse wave coincide with an amplitude and a wavelength of said normal pulse wave, said indication control means controlling said display device to indicate the waveforms of said normal pulse wave and said abnormal pulse wave which have been normalized by said normalizing means, such that said waveforms of said normal pulse wave and said abnormal pulse wave are superimposed on each other.

7. A physical information monitor system according to claim 6, wherein said physical information obtaining means obtains as said physical information a series of pulses of a pulse wave generated in synchronism with heartbeat of said subject, while said indication control means controls said display device to indicate a series of pulses of a normal pulse wave previously obtained in the comparatively normal condition of said subject and said series of pulses of the pulse wave obtained by said physical information obtaining means in an abnormal condition of said subject, in a same two-dimensional coordinate system in which time is taken along an abscissa while an amplitude of said series of pulses is taken along an ordinate.

8. A physical information monitor system according to claim 6, wherein said indication control means includes calculating means for calculating an area difference index which quantitatively indicates a difference between an area defined by said waveform of said normal pulse wave and an area defined by said waveform of said abnormal pulse wave, said indication control means controlling said display device to indicate said area difference calculated by said calculating means.

* * * * *